(12) United States Patent
Justis

(10) Patent No.: US 9,066,770 B2
(45) Date of Patent: Jun. 30, 2015

(54) SURGICAL DELIVERY INSTRUMENT AND METHOD

(75) Inventor: Jeff R. Justis, Germantown, TN (US)

(73) Assignee: Warsaw Orthopedics, Inc., Warsaw, IN (US)

( * ) Notice: Subject to any disclaimer, the term of this patent is extended or adjusted under 35 U.S.C. 154(b) by 485 days.

(21) Appl. No.: 12/906,608

(22) Filed: Oct. 18, 2010

(65) Prior Publication Data

US 2012/0095417 A1 Apr. 19, 2012

(51) Int. Cl.
| | |
|---|---|
| A61B 17/84 | (2006.01) |
| A61B 17/86 | (2006.01) |
| A61B 17/88 | (2006.01) |
| A61B 17/16 | (2006.01) |
| A61B 19/00 | (2006.01) |

(52) U.S. Cl.
CPC ......... *A61B 17/8897* (2013.01); *A61B 17/1604* (2013.01); *A61B 2019/306* (2013.01)

(58) Field of Classification Search
USPC ................ 606/96, 104, 60, 80, 184, 79, 108; 604/164, 0.01, 272, 164.1, 164.12, 604/164.13
See application file for complete search history.

(56) References Cited

U.S. PATENT DOCUMENTS

| | | | |
|---|---|---|---|
| 4,204,541 A * | 5/1980 | Kapitanov | ..................... 606/145 |
| 4,706,671 A * | 11/1987 | Weinrib | ......................... 606/159 |
| 5,090,956 A | 2/1992 | McCoy | |
| 5,211,183 A | 5/1993 | Wilson | |
| 5,662,683 A * | 9/1997 | Kay | ............................... 606/232 |
| 5,810,857 A * | 9/1998 | Mackool | ....................... 606/167 |
| 5,904,657 A | 5/1999 | Unsworth et al. | |
| 7,316,655 B2 | 1/2008 | Garibotto et al. | |
| 7,455,737 B2 | 11/2008 | Boismier et al. | |
| 7,651,496 B2 | 1/2010 | Keegan et al. | |
| 2002/0123698 A1 | 9/2002 | Garibotto et al. | |
| 2007/0021685 A1 | 1/2007 | Oepen et al. | |
| 2007/0123913 A1 | 5/2007 | Beulke et al. | |
| 2008/0045863 A1 | 2/2008 | Bakos | |
| 2008/0255555 A1 | 10/2008 | Justis et al. | |
| 2009/0187116 A1* | 7/2009 | Noishiki et al. | .............. 600/564 |
| 2009/0198153 A1 | 8/2009 | Shriver | |
| 2009/0264834 A1 | 10/2009 | Scheurmann | |

FOREIGN PATENT DOCUMENTS

WO WO2008005618 * 1/2008 ............ A61M 25/06

* cited by examiner

*Primary Examiner* — Nicholas Woodall
(74) *Attorney, Agent, or Firm* — Sorell Lenna & Schmidt LLP

(57) ABSTRACT

A surgical instrument includes a needle extending between a proximal end and a distal end. The needle defines a longitudinal axis. The needle includes an elongated cavity that defines an opening disposed proximal to the distal end. A wire extends between a proximal end and a distal end configured for fixation with tissue. The wire is configured for movable disposal within the cavity. The distal end of the wire includes a retainer configured to prevent advancement of the retainer within the tissue. Methods of use are disclosed.

11 Claims, 18 Drawing Sheets

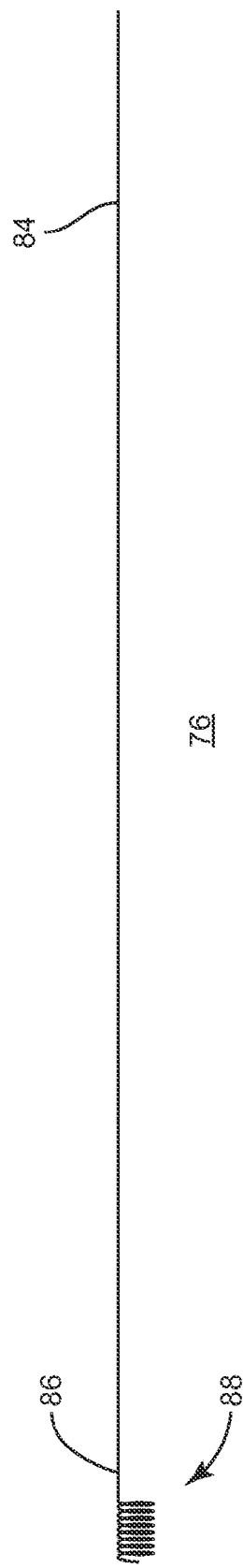
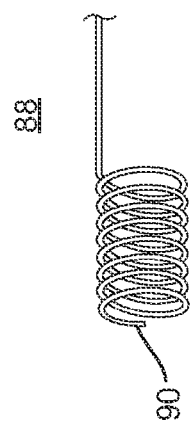
FIG. 6
FIG. 7

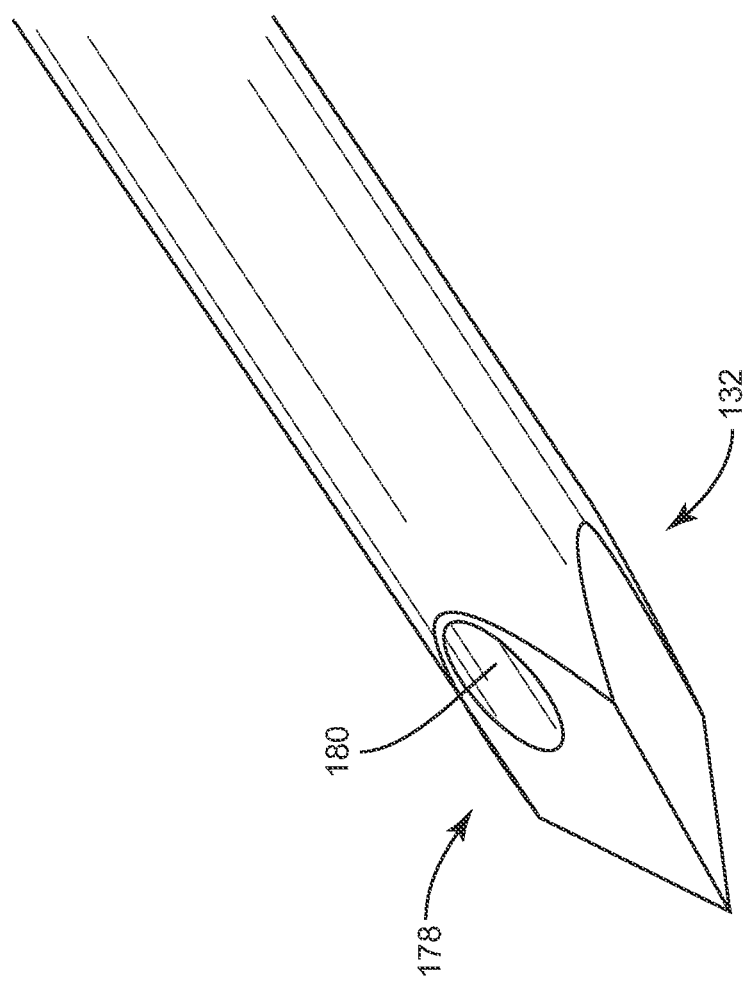

US 9,066,770 B2

SURGICAL DELIVERY INSTRUMENT AND METHOD

TECHNICAL FIELD

The present disclosure generally relates to medical devices for the treatment of musculoskeletal disorders, and more particularly to a surgical delivery instrument and method, which include a needle having a guide wire for advancing surgical components and being configured to prevent undesired advancement within tissue.

BACKGROUND

Spinal disorders such as degenerative disc disease, disc herniation, osteoporosis, spondylolisthesis, stenosis, scoliosis and other curvature abnormalities, kyphosis, tumor, and fracture may result from factors including trauma, disease and degenerative conditions caused by injury and aging. Spinal disorders typically result in symptoms including pain, nerve damage, and partial or complete loss of mobility.

Non-surgical treatments, such as medication, rehabilitation and exercise can be effective, however, may fail to relieve the symptoms associated with these disorders. Surgical treatment of these spinal disorders includes fusion, fixation, discectomy, laminectomy and implantable prosthetics. Fusion and fixation treatment may employ implants such as interbody fusion devices to achieve arthrodesis. Implants may also be used in other treatments such as arthroplasty. Surgical treatments employing minimally invasive techniques may use a guide wire for advancing an implant to a surgical site. This disclosure describes an improvement over these prior art technologies.

SUMMARY OF THE INVENTION

Accordingly, a surgical delivery instrument and related methods are provided for treating musculoskeletal disorders. It is contemplated that the surgical delivery instrument and methods disclosed include a needle having a guide wire for advancing surgical components. It is further contemplated that the guide wire is configured to prevent undesired advancement within tissue.

In one particular embodiment, in accordance with the principles of the present disclosure, a surgical instrument is provided. The surgical instrument includes a needle extending between a proximal end and a distal end. The needle defines a longitudinal axis. The needle includes an elongated cavity that defines an opening disposed proximal to the distal end. A wire extends between a proximal end and a distal end configured for fixation with tissue. The wire is configured for movable disposal within the cavity. The distal end of the wire includes a retainer configured to prevent advancement of the retainer within the tissue.

In one embodiment, the surgical instrument includes a guide wire extending between a proximal end and a distal end. The guide wire is configured for slidable movement within the elongated cavity. The distal end of the guide wire includes a flexible anchor. The flexible anchor is movable between a first orientation and a second orientation such that the anchor is expanded for removable fixation with tissue and in a configuration to prevent further advancement of the anchor within the tissue.

In one embodiment, the surgical instrument includes the needle including an outer surface that defines an open groove including an opening disposed proximal to the distal end. The needle includes a guide wire configured for slidable movement within the groove. The guide wire extends between a proximal end and a distal end. The distal end includes a flexible anchor having a blunt tip. A sleeve is disposed about the needle. An actuator is connected to the needle and the sleeve to effect movement of the anchor between a first orientation such that the anchor is disposed in a collapsed configuration with the needle and a second, deployed orientation such that the anchor is expanded for fixation with tissue. The blunt tip is disposed to prevent further advancement of the anchor within the tissue.

BRIEF DESCRIPTION OF THE DRAWINGS

The present disclosure will become more readily apparent from the specific description accompanied by the following drawings, in which:

FIG. 6 is a side view of a wire of the surgical instrument shown in FIG. 1;

FIG. 7 is an enlarged, side cutaway view of a retainer of the wire shown in FIG. 6;

FIG. 16 is an enlarged, cutaway perspective view of one embodiment of a distal end of the needle of the surgical instrument shown in FIG. 1;

Like reference numerals indicate similar parts throughout the figures.

DETAILED DESCRIPTION OF THE INVENTION

Figure 1:
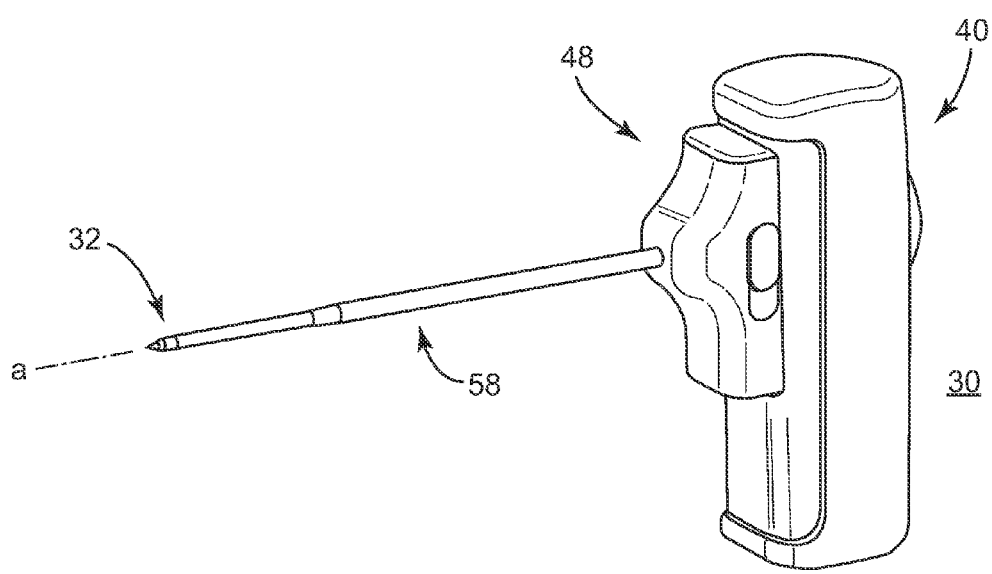
FIG. 1 is a perspective view of one embodiment of a surgical instrument in accordance with the principles of the present disclosure.
Figure 2:
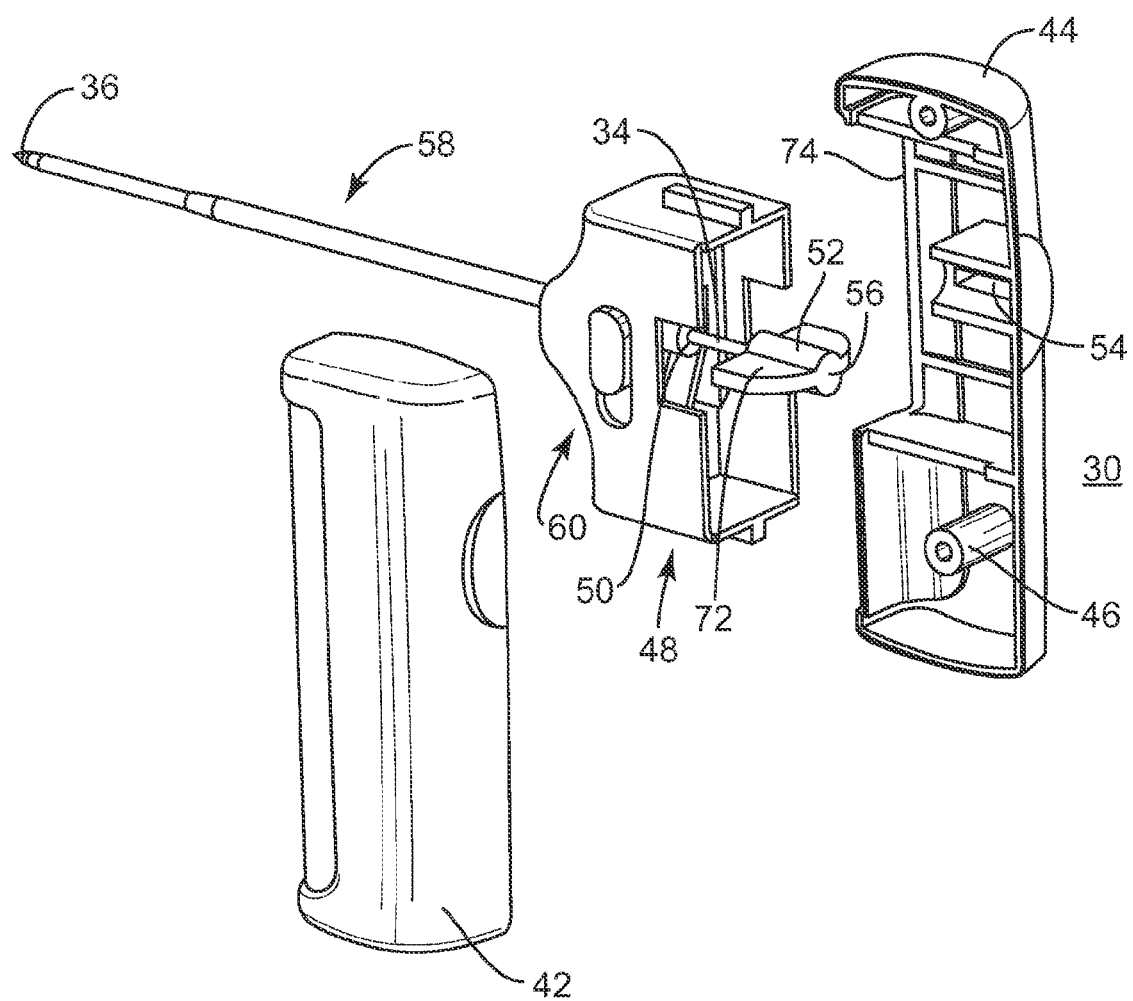
FIG. 2 is a perspective view of the surgical instrument shown in FIG. 1 with parts separated.
Figure 3:
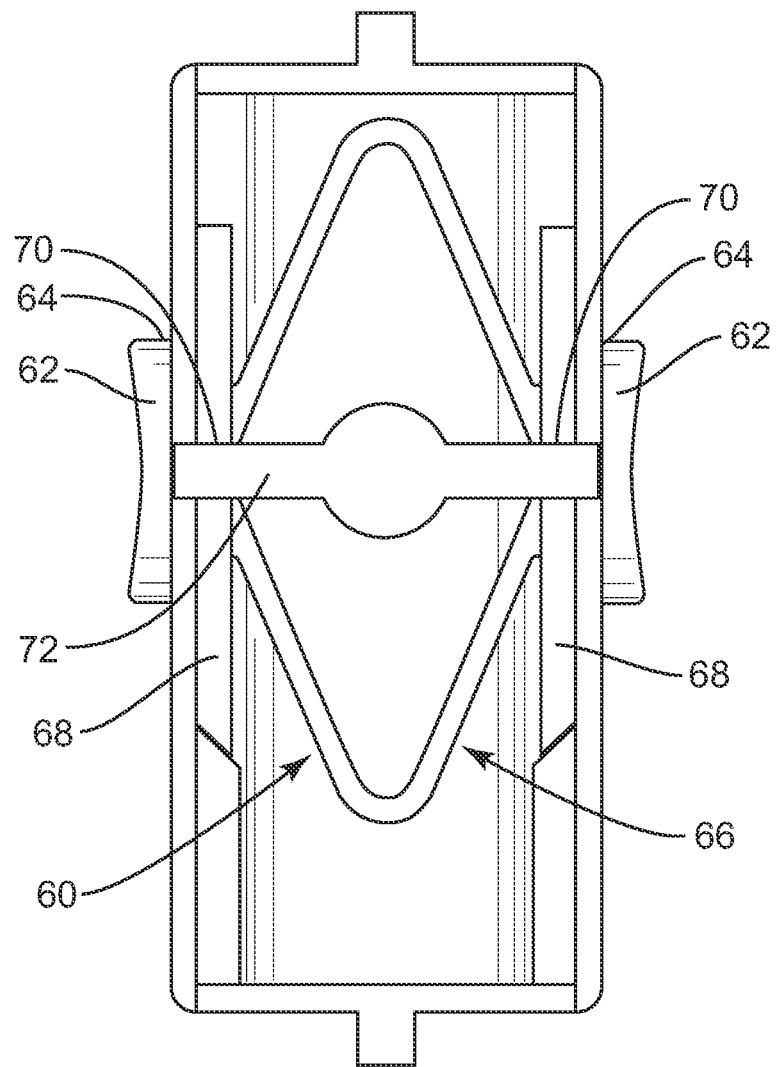
FIG. 3 is a plan view in cross section of the surgical instrument shown in FIG. 1.

The exemplary embodiments of the surgical delivery instrument and related methods of use disclosed are discussed in terms of medical devices for the treatment of musculoskeletal disorders and more particularly, in terms of a surgical delivery instrument and method. The surgical delivery instrument includes a needle having a guide wire for advancing surgical components. The guide wire has a distal end that is configured to prevent undesired advancement of the guide wire within tissue. It is envisioned that the surgical delivery instrument and methods of use disclosed prevent unintended injury to the body of a patient with a guide wire that eliminates undesired advancement within tissue during delivery of surgical components to a surgical site. It is further envisioned that the surgical delivery instrument is configured to deliver various surgical components such as, for example, implants, drills and other tools. The surgical delivery instrument and method may be employed with an imaging or surgical navigation system.

It is envisioned that the present disclosure may be employed to treat spinal disorders such as, for example, degenerative disc disease, disc herniation, osteoporosis, spondylolisthesis, stenosis, scoliosis and other curvature abnormalities, kyphosis, tumor and fractures. It is contemplated that the present disclosure may be employed with other osteal and bone related applications, including those associated with diagnostics and therapeutics. It is further contemplated that the disclosed surgical delivery instrument may be employed in a surgical treatment with a patient in a prone or supine position, and/or employ various surgical approaches to the spine, including anterior, posterior, posterior mid-line, lateral, postero-lateral, and/or antero-lateral approaches, and in other body regions. The present disclosure may also be alternatively employed with procedures for treating the lumbar, cervical, thoracic and pelvic regions of a spinal column. The system and methods of the present disclosure may also be used on animals, bone models and other non-living substrates, such as, for example, in training, testing and demonstration.

The present invention may be understood more readily by reference to the following detailed description of the invention taken in connection with the accompanying drawing figures, which form a part of this disclosure. It is to be understood that this invention is not limited to the specific devices, methods, conditions or parameters described and/or shown herein, and that the terminology used herein is for the purpose of describing particular embodiments by way of example only and is not intended to be limiting of the claimed invention. Also, as used in the specification and including the appended claims, the singular forms "a," "an," and "the" include the plural, and reference to a particular numerical value includes at least that particular value, unless the context clearly dictates otherwise. Ranges may be expressed herein as from "about" or "approximately" one particular value and/or to "about" or "approximately" another particular value. When such a range is expressed, another embodiment includes from the one particular value and/or to the other particular value. Similarly, when values are expressed as approximations, by use of the antecedent "about," it will be understood that the particular value forms another embodiment. It is also understood that all spatial references, such as, for example, horizontal, vertical, top, upper, lower, left and right, are for illustrative purposes only and can be varied within the scope of the disclosure. For example, the references "upper" and "lower" are relative and used only in the context to the other, and are not necessarily "superior" and "inferior".

The following discussion includes a description of a surgical delivery instrument and related methods of employing the surgical delivery instrument in accordance with the principles of the present disclosure. Alternate embodiments are also disclosed. Reference will now be made in detail to the exemplary embodiments of the present disclosure, which are illustrated in the accompanying figures. Turning now to FIGS. 1-8, there is illustrated components of a surgical delivery instrument 30 in accordance with the principles of the present disclosure.

The components of surgical delivery instrument 30 are fabricated from materials suitable for medical applications, including metals, polymers, ceramics, biocompatible materials and/or their composites, depending on the particular application and/or preference of a medical practitioner. For example, the components of surgical delivery instrument 30, individually or collectively, and which may be monolithically formed or integrally connected, can be fabricated from materials such as stainless steel, stainless steel alloys, titanium, titanium alloys, super-elastic titanium alloys, cobalt-chrome alloys, shape memory materials, such as super-elastic metallic alloys (e.g., Nitinol, super-elastic plastic metals, such as GUM METAL® manufactured by Toyotsu Material Incorporated of Japan), thermoplastics such as polyaryletherketone (PAEK) including polyetheretherketone (PEEK), polyetherketoneketone (PEKK) and polyetherketone (PEK), carbon-PEEK composites, PEEK-BaSO$_4$ polymeric rubbers, biocompatible materials such as polymers including plastics, metals, ceramics and composites thereof, rigid polymers including polyphenylene, polyamide, polyimide, polyetherimide, polyethylene, and epoxy. Various components of surgical delivery instrument 30 may have material composites, including the above materials, to achieve various desired characteristics such as strength, rigidity, elasticity, compliance, biomechanical performance, durability and radiolucency or imaging preference.

Surgical delivery instrument 30 is configured to deliver surgical components to a surgical site at a desired location and trajectory to perform a surgical treatment. Surgical delivery instrument 30 includes a needle 32 extending between a proximal end 34 and a distal end 36. Needle 32 defines a longitudinal axis a and an outer surface 38. Needle 32 has a smooth or even outer surface 38 and a cylindrical cross-section. It is envisioned that the outer surface of needle 32 may be rough, textured, porous, semi-porous, dimpled and/or polished. It is further envisioned that the cross-sectional geometry of needle 32 may have various configurations, such as, for example, round, oval, oblong, triangular, polygonal, irregular, uniform, non-uniform, consistent or variable. Distal end 36 has a sharpened configuration for penetrating tissue. It is contemplated that tissue includes soft tissue, cartilage and/or bone.

Proximal end 34 is connected to a handle 40 configured for manipulation by a medical practitioner during use. Handle 40 includes a first section 42 and a second section 44 that are assembled via posts 46 to support an actuator, such as, for example, a trigger housing 48. Housing 40 has a substantially cylindrical cross-section configured for gripping by a medical practitioner. It is contemplated that handle 40 may have other cross-sectional geometries such as those described herein.

Trigger housing 48 defines a passageway 50 for slidable support of needle 32 to facilitate movement of needle 32 relative thereto.

A stop 52 is mounted with proximal end 34 and is disposed within a cavity 54 defined by handle 40 upon assembly of sections 42, 44. Stop 52 has a planar surface 56 for engaging an interior surface of handle 40, as will be described. A sleeve 58 is mounted to trigger housing 48 and is disposed about outer surface 38 for slidable support of needle 32 and to facilitate relative movement thereto. It is envisioned that the inner cross sectional geometry of sleeve 58 corresponds to the outer surface of needle 32.

Handle 40 includes a safety element, such as, for example, a slide 60 configured to prevent undesired or inadvertent actuation of needle 32. Slide 60 includes opposing buttons 62 mounted in cavities 64 of trigger housing 48. Buttons 62 are connected with resiliently biased spring element 66 mounted within trigger housing 48 by locks 68, which define slots 70 that are configured to facilitate actuation of needle 32.

Upon assembly of handle 40, stop 52 includes wings 72 that are disposed within cavities 54. In a first position (FIG. 1), buttons 62 are in an upward orientation and slots 70 are out of alignment with wings 72 such that needle 32 is in a first position and prevented from forward advancement.

Figure 11:
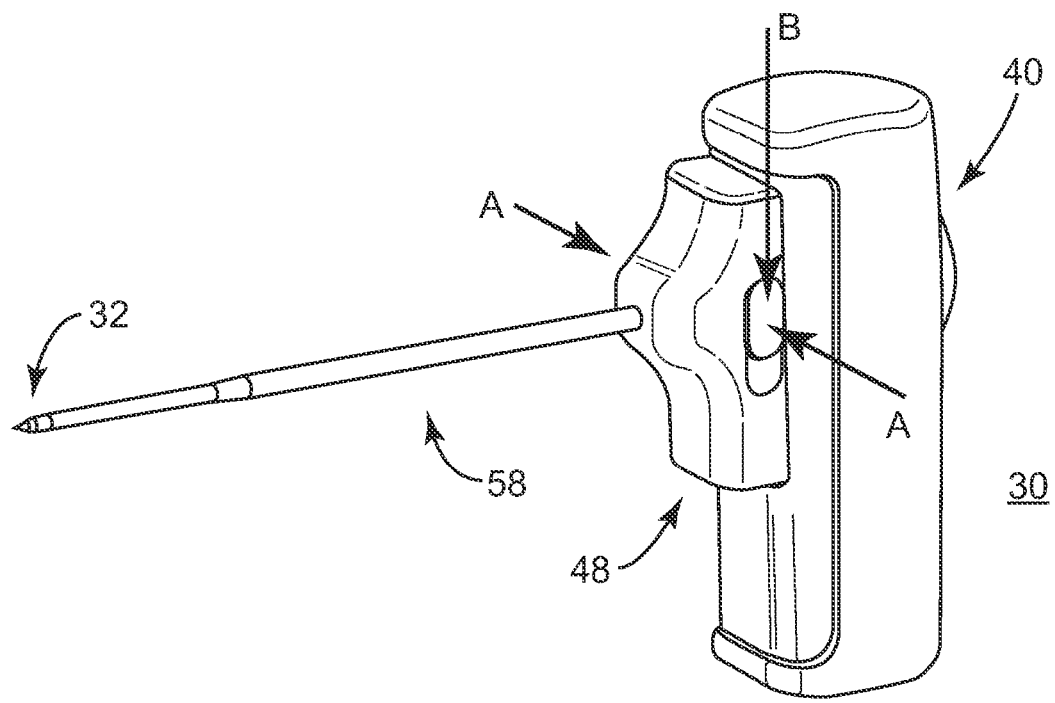
FIG. 11 is a perspective view of the surgical instrument shown in FIG. 1.
Figure 12:
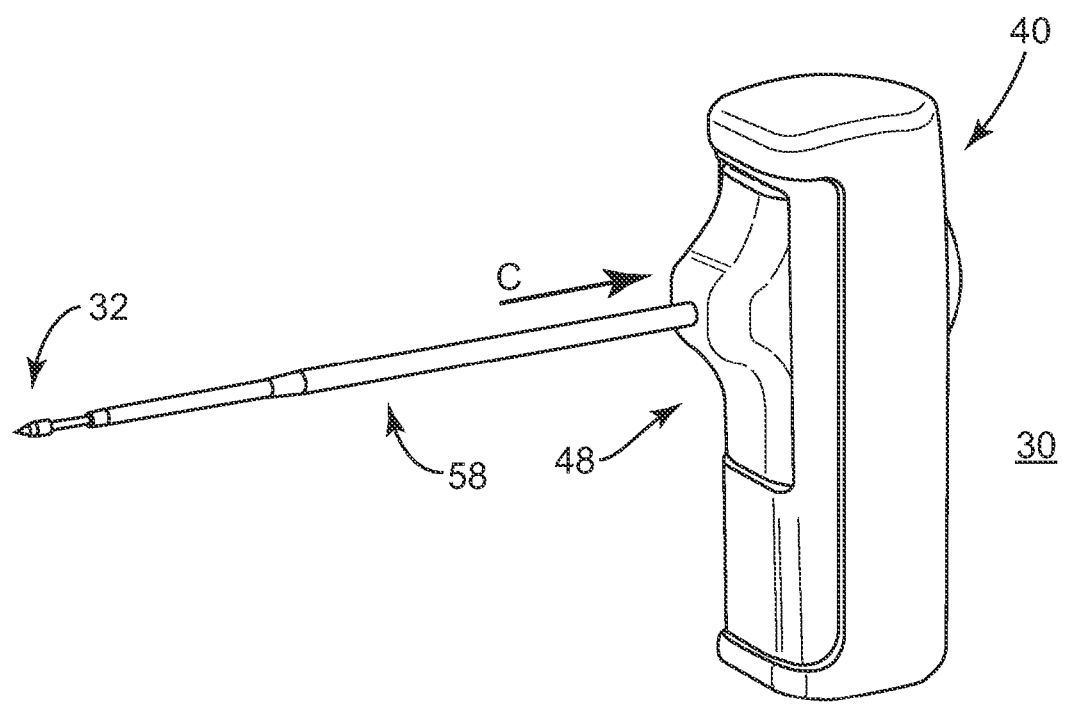
FIG. 12 is a perspective view of the surgical instrument shown in FIG. 11.

In a second position (FIG. 11), buttons 62 are manipulated against the bias of spring element 66, in the direction shown by arrows A, and slid in the direction shown by arrow B, downward such that locks 68 slide and slots 70 are brought into alignment with wings 72 such that needle 32 is released and advanceable for actuation, as will be described. Trigger housing 48 is manipulated and/or squeezed, in the direction shown by arrow C in FIG. 12, within a cavity 74 of handle 40 to actuate needle 32 from a first position (FIGS. 4, 11) to a second position (FIGS. 5, 12).

Needle 32 includes a guide wire 76 configured for relative slidable movement within an elongated cavity, such as, for example, a open groove 78 of needle 32. Open groove 78 defines an opening 80 disposed proximal to distal end 36. Groove 78 also defines an opening (not shown) adjacent proximal end 34 configured to receive guide wire 76 and facilitate loading of guide wire 76 with needle 32 in trigger housing 48. Guide wire 76 is advanced along groove 78 for assembly therewith. It is contemplated that this loading configuration of needle 32 and guide wire 76 facilitates reuse of surgical delivery instrument 30 including guide wire 76 including multiple reuse. It is further contemplated that surgical delivery instrument 30 or one or a plurality of its components are disposable. Groove 78 is non-coaxial with longitudinal axis a.

Guide wire 76 is configured for slidable movement within groove 78 relative to needle 32. Guide wire 76 extends along groove 78 and through opening 80. Guide wire 76 extends between a proximal end 84 and a distal end 86. Distal end 86 includes a retainer, such as, for example, a flexible anchor 88. Anchor 88 is configured for fixation with tissue and includes a tip 90. Tip 90 has a blunt configuration and prevents undesired advancement of anchor 88 within tissue. It is contemplated that anchor 88 is temporarily and/or removably fixed with tissue. It is further contemplated that anchor 88 may be implantable with tissue.

Needle 32 defines a reduced diameter portion 92 disposed between distal end 36 and opening 80. Reduced diameter portion 92 is configured for disposal of anchor 88. Anchor 88 has a helical coil configuration that is disposed circumferentially about reduced diameter portion 92.

Figure 4:
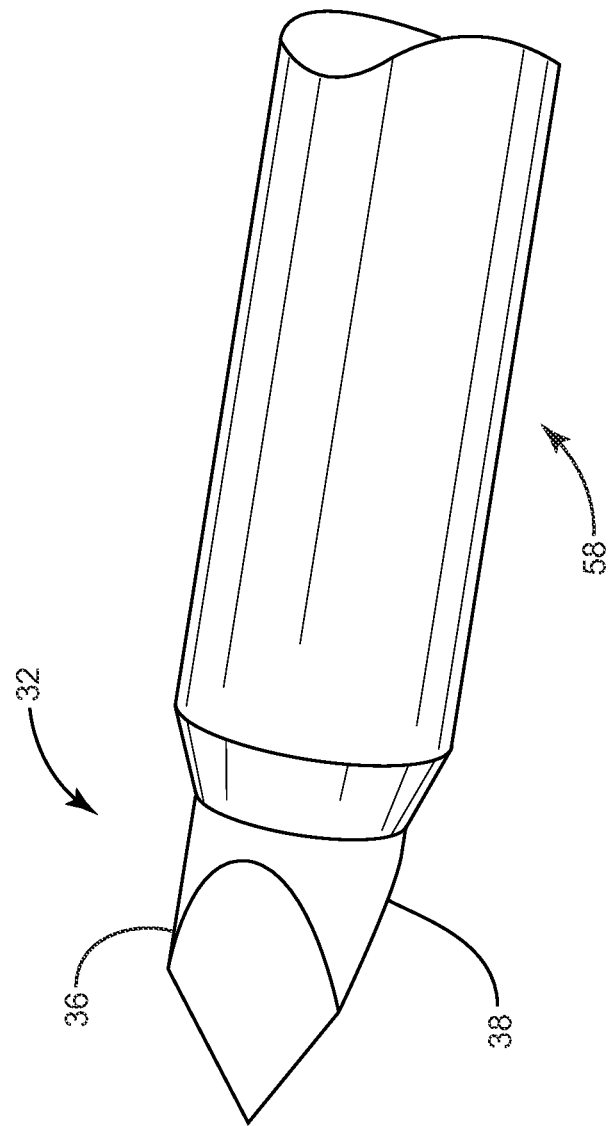
FIG. 4 is an enlarged, perspective view of a distal end of the surgical instrument shown in FIG. 1.
Figure 5:
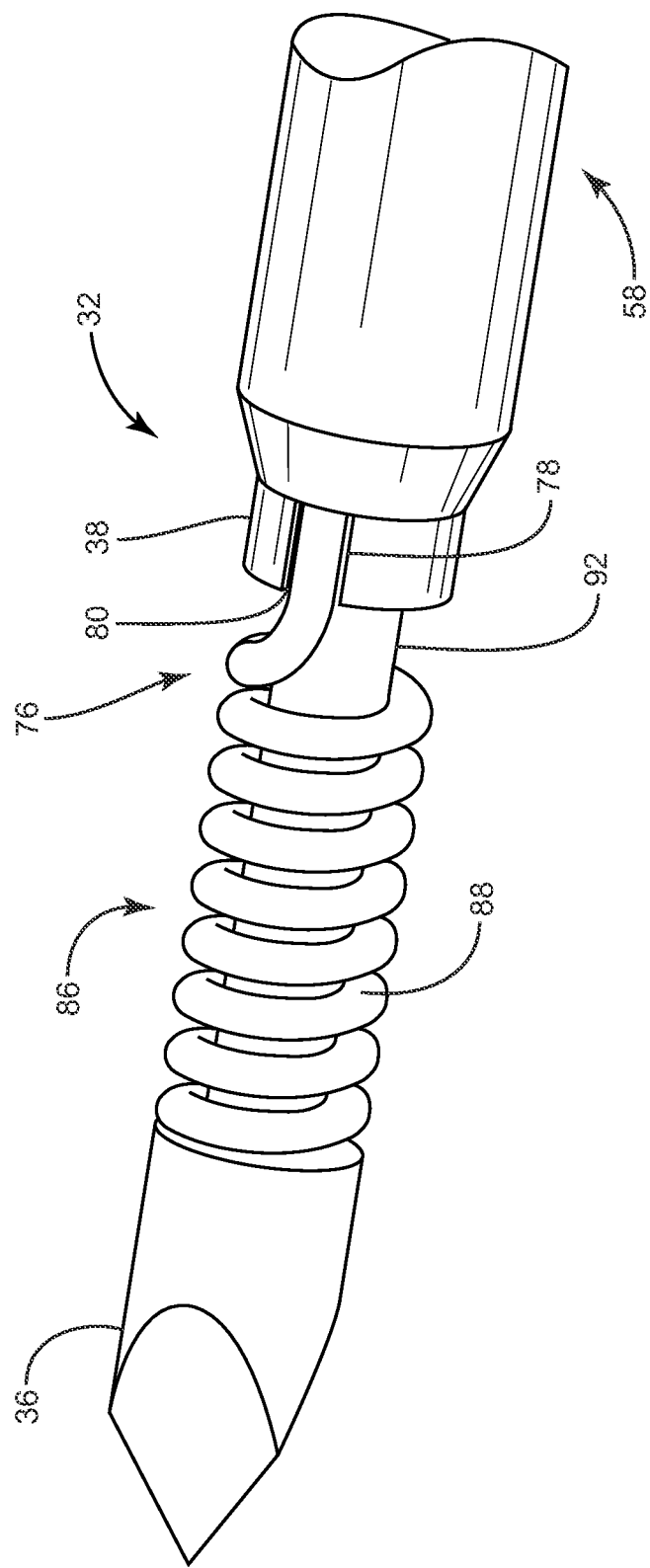
FIG. 5 is an enlarged, perspective view of the distal end of the surgical instrument shown in FIG. 1.
Figure 8:
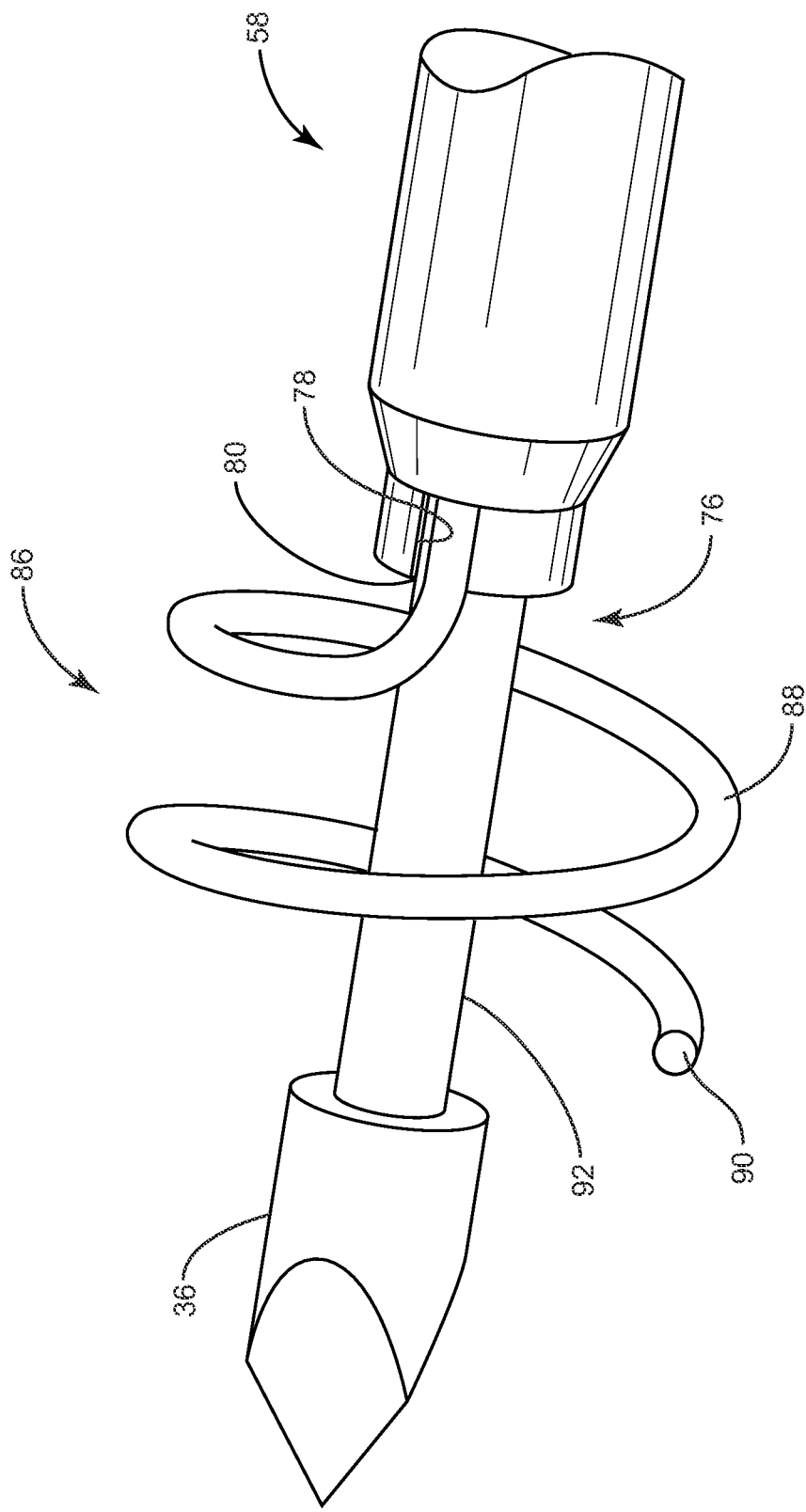
FIG. 8 is an enlarged, perspective view of the distal end of the surgical instrument shown in FIG. 1.

In the first position of needle 32, as shown in FIG. 4, anchor 88 is disposed about reduced diameter portion 92 in a first orientation (FIG. 5) such that anchor 88 is in an unexpanded, collapsed configuration. Anchor 88 is fixed with needle 32 and prevented from disengagement with reduced diameter portion 92 due to its collapsed configuration. Anchor 88 is flexible and movable, via actuation from and manipulation of guide wire 76 with handle 40 and trigger housing 48, between the first orientation and a second, deployed orientation, as shown in FIG. 8. As needle 32 is actuated and moved to its second position, as shown in FIG. 5, anchor 88 is disposed about reduced diameter portion 92 and is in the first orientation. Distal end 86 extends beyond sleeve 58 and anchor 88 remains collapsed and unexpanded.

Needle 32 is rotated via manipulation of handle 40 and/or trigger housing 48 such that tip 90 engages tissue. Further rotation of needle 32 generates a resistive force transmitted through the coil of anchor 88, due to the corresponding rotation of guide wire 76 and engagement of tip 90 with tissue, which in turn causes anchor 88 to expand radially outward from reduced diameter portion 92. Anchor 88 expands to the second orientation, as shown in FIG. 8, and the outer surface of the coil configuration of anchor 88 frictionally engages the tissue such that guide wire 76 is disposed in a fixed position with the tissue at a desired location at the surgical site. Blunt tip 90 prevents further advancement of distal end 86 within the tissue.

Needle 32 is removable from guide wire 76 such that distal end 36 can pass through anchor 88 in the second orientation, away from the surgical site. Guide wire 76 passes through groove 78 and disengages therefrom via exiting from opening 80. Surgical components can be advanced to the surgical site over guide wire 76 at a desired location and trajectory, as will be described.

It is contemplated that anchor 88 is removably fixed with tissue and is movable from the second orientation to the first orientation to disengage from the tissue. Upon completion of a surgical treatment, adjustment of guide wire 76 and/or other uses, guide wire 76 is rotated in an opposing direction to relieve the tension in distal end 86 associated with the resistive force generated to force anchor 88 to the first orientation. Anchor 88 collapses and anchor 88 returns to the first second orientation. It is envisioned that anchor 88 has a shape memory configuration to facilitate movement of anchor 88 between the first orientation and the second orientation, for example, fabrication from a shape memory material, such as those described herein.

As anchor 88 collapses to the first orientation, the outer surface of anchor 88 is released from frictional engagement with the tissue. Guide wire 76 is removed from or adjusted within the surgical site. In one embodiment, anchor 88 collapses and returns to the first orientation for disposal about reduced diameter portion 92. With anchor 88 being coiled about reduced diameter portion 92 in the first orientation, needle 32 is manipulated to its first position within sleeve 58.

It is contemplated that all of guide wire 76 or only a portion thereof, such as, for example, anchor 88 has a smooth or even surface. It is further contemplated that all or only a portion of guide wire 76 may have an outer surface that is rough, textured, dimpled and/or polished. Guide wire 76 has a substantially cylindrical cross-section. It is envisioned that all or only portion of guide wire 76 may have various cross-sectional geometries such as those described herein. It is further envisioned that portions of guide wire 76 many have rigid, flexible and/or a shape memory configuration.

In assembly, operation and use, surgical delivery instrument 30 is assembled as described above and employed with a minimally invasive surgical procedure with a section of a spine of a patient. Guide wire 76 facilitates advancement and positioning of surgical components to a surgical site within the patient's body. It is envisioned that surgical delivery instrument 30 may be employed for performing spinal surgeries, such as, for example, discectomy, laminectomy, fusion, laminotomy, laminectomy, nerve root retraction, foramenotomy, facetectomy, decompression, spinal nucleus or disc replacement, bone graft and implantation of prosthetics including plates, rods, and bone engaging fasteners used in any existing surgical method or technique including open surgery, mini-open surgery, minimally invasive surgery and percutaneous surgical implantation.

For example, surgical delivery instrument 30 is employed with a percutaneous approach for treating the spine section. A cannula, mini-open retractor, tube, a sleeve for slidable support of sleeve 58, only sleeve 58 and/or an incision provides a protected passageway for surgical delivery instrument 30 such that surgical components can be advanced over guide wire 76 to the surgical site. A medical practitioner will make an incision in the skin of a patient's body to create a protected passageway 94 over and in approximate alignment with vertebrae V at the surgical site. A sleeve or other dilator may be employed to separate the muscles and tissues to create passageway 94 through which the surgery may be performed. Passageway 94 allows for the insertion and use of surgical delivery instrument 30. It is contemplated that sleeve 58 may be configured as an in-situ guidance instrument and may include an endoscope camera tip.

Passageway 94 is created and extends from the incision to adjacent vertebrae V. A bore 96 is pre-drilled in tissue, such as, for example, bone of vertebrae V prior to insertion of sleeve 58. Bore 96 is configured to receive distal end 36. It is envisioned that passageway 94 is disposed at various angular orientations relative to vertebrae V. It is further envisioned that passageway 94 may extend outside a patient's body using various instruments as described herein.

Figure 9:
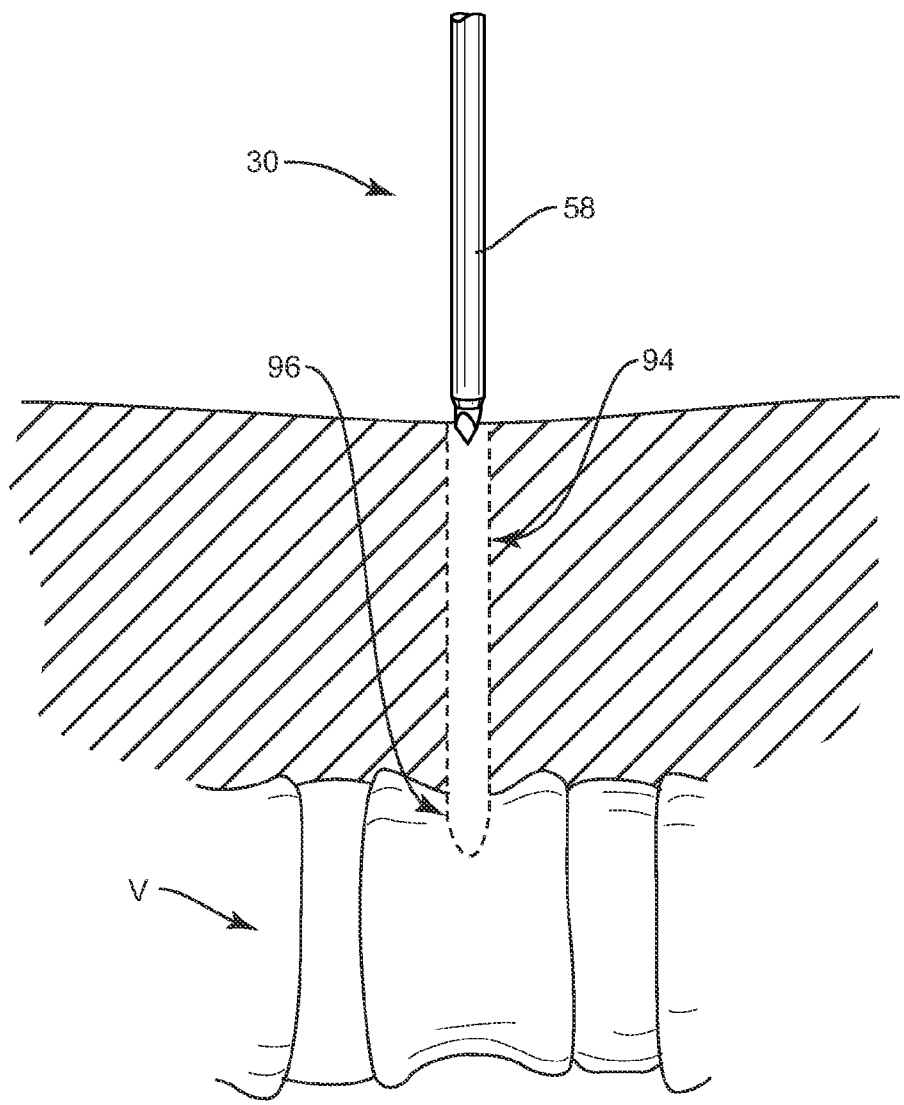
FIG. 9 is a side view in part cross section of the surgical instrument shown in FIG. 1 and a surgical site of a body.

Surgical delivery instrument 30 is inserted within passageway 94, as shown in FIG. 9. Sleeve 58 is inserted along passageway 94, and distal end 36 is forced into bore 96 and into engagement with an end portion thereof. Needle 32 is disposed in its first position (FIG. 4). Buttons 62 are depressed in the direction shown by arrows A and slid in the direction shown by arrow B such that needle 32 is released and advanceable for actuation, as shown in FIG. 11 and described above.

Figure 10:
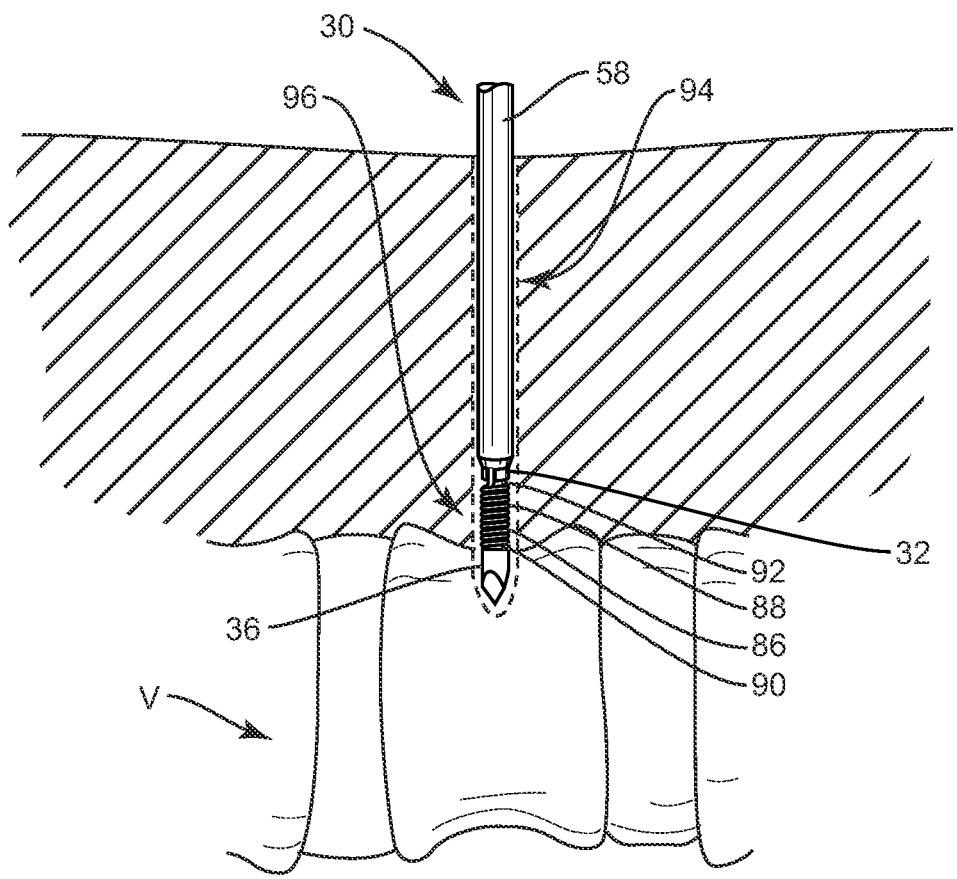
FIG. 10 is a side view in part cross section of the surgical instrument and the surgical site shown in FIG. 9.
Figure 13:
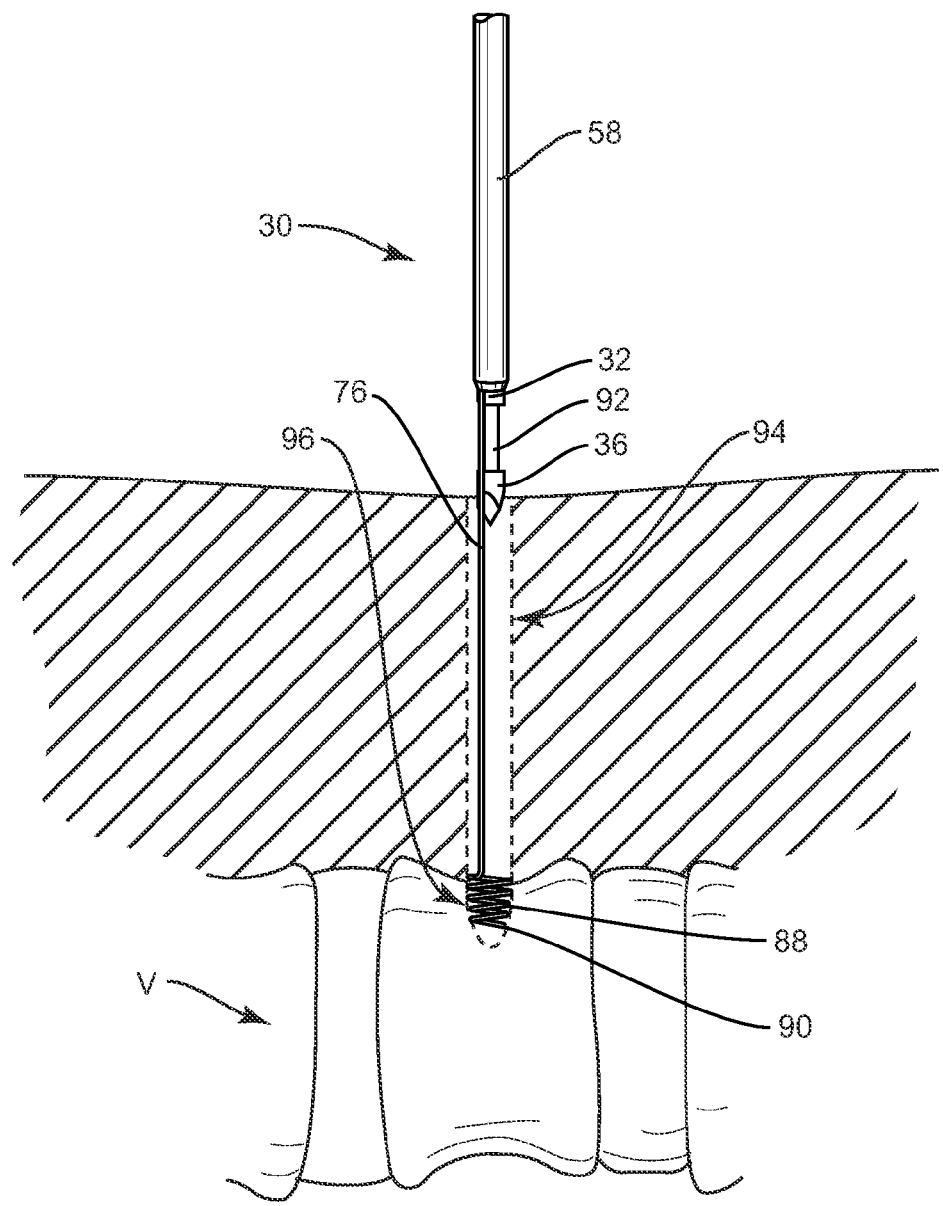
FIG. 13 is a side view in part cross section of the surgical instrument and the surgical site shown in FIG. 10.
Figure 14:
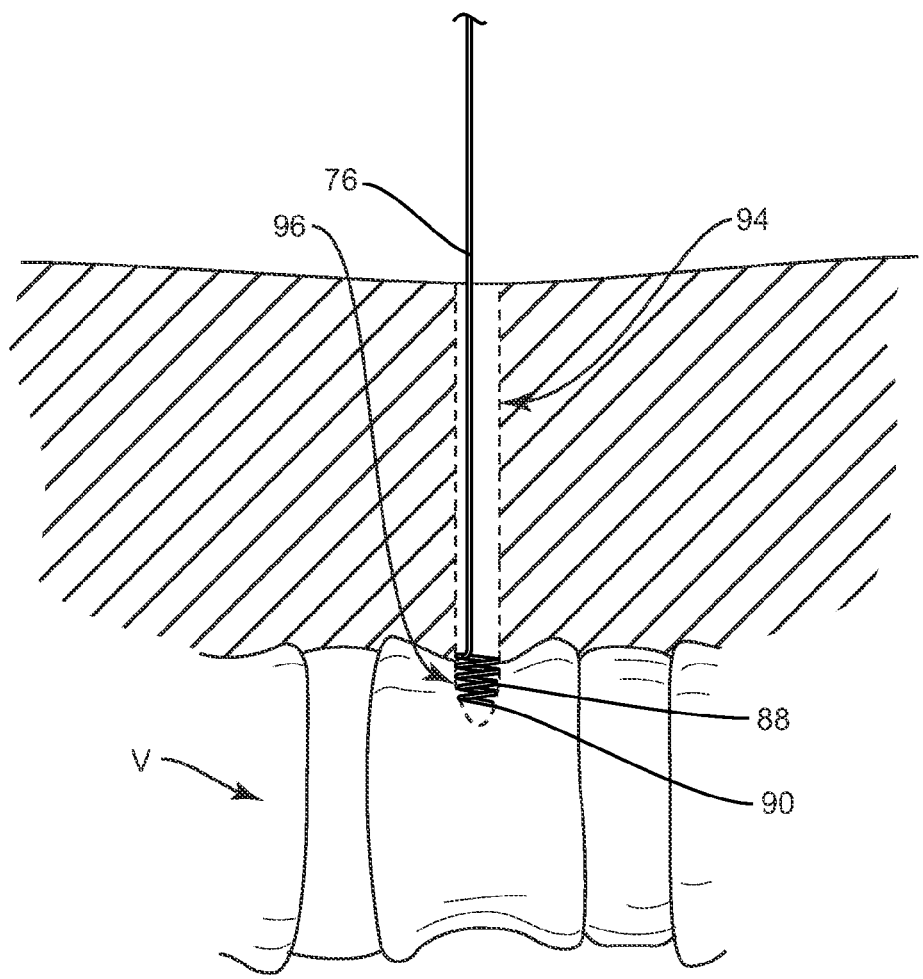
FIG. 14 is a side view in part cross section of the wire shown in FIG. 6 and the surgical site shown in FIG. 13.

Trigger housing 48 is manipulated in the direction shown by arrow C to actuate needle 32 from its first position to its second position, as shown in FIGS. 10 and 12, and described above. Anchor 88 is disposed about reduced diameter portion 92 and in its first orientation. Distal end 86 extends beyond sleeve 58 and anchor 88 remains collapsed and unexpanded. Needle 32 is rotated such that tip 90 engages tissue, such as, for example, bone of vertebrae V, which causes anchor 88 to deploy and expand radially outward, as described above, to its second orientation, as shown in FIG. 13. The outer surface of the coil configuration of anchor 88 frictionally engages the bone such that guide wire 76 is disposed in a fixed position with vertebrae V at the desired location at the surgical site. Blunt tip 90 prevents further advancement of guide wire 76 in the bone, as shown in FIG. 14.

Needle 32 is removable from guide wire 76 as described above. Surgical components are advanced to the surgical site over guide wire 76 at a desired location and trajectory of the surgical site for the surgical procedure. Upon advancement of the desired surgical components to the surgical site, adjustment of surgical delivery instrument 30 and/or completion of the surgical procedure, anchor 88 is moved from its second orientation to the first orientation.

Figure 15:
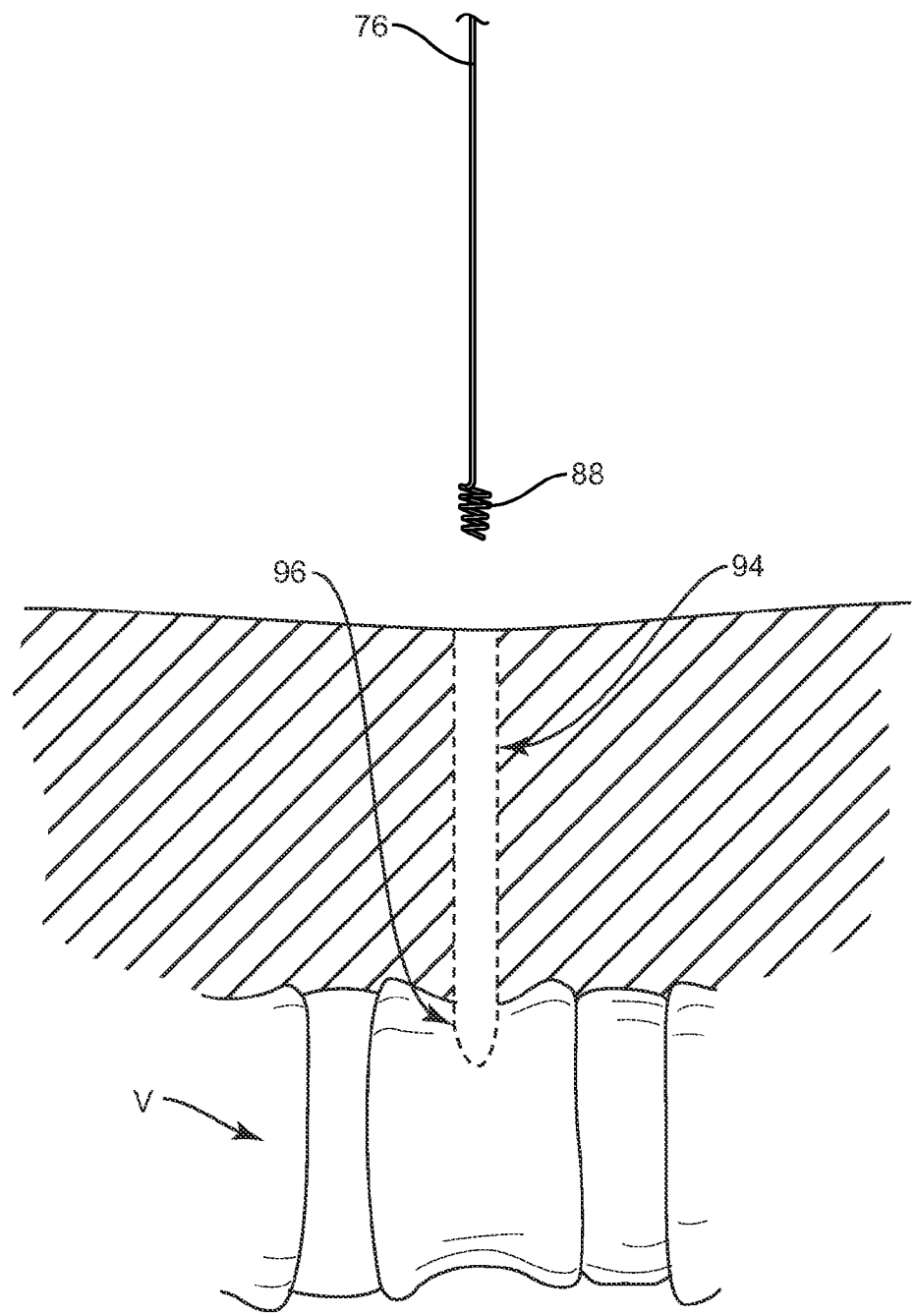
FIG. 15 is a side view in part cross section of the wire and the surgical site shown in FIG. 14.

Guide wire 76 is rotated to force anchor 88 to its first orientation. Anchor 88 collapses and returns to the first orientation such that the outer surface of anchor 88 is released from frictional engagement with the bone and bore 96. Guide wire 76 is removed from passageway 94, as shown in FIG. 15.

In one embodiment, guide wire 76 is employed to advance implants, such as, for example, bone screws and rods (not shown) to the surgical site. Upon completion of treatment and/or desired removal of instrument 30, the coil portion of anchor 88 may be pulled or withdrawn through a cannulated portion of the implant such that anchor 88 elastically deforms (shape memory) into the cannulation of the implant or other surgical component and reform into its first orientation upon exiting the cannulated portion.

It is envisioned that the use of microsurgical and image guided technologies may be employed to access, view and repair spinal deterioration or damage, with the aid of surgical delivery instrument 30. Upon completion of the procedure, surgical delivery instrument 30 is removed and the incision is closed. It is contemplated that a surgical procedure employing surgical delivery instrument 30 may be used with various surgical components, such as, for example, implants, surgical tools and surgical instruments, such as, rasps, curettes, nerve root retractors, tissue retractors, forceps, cutter, drills, scrapers, reamers, separators, rongeurs, taps, cauterization instruments, irrigation and/or aspiration instruments, illumination instruments and/or inserter instruments.

Figure 17A:
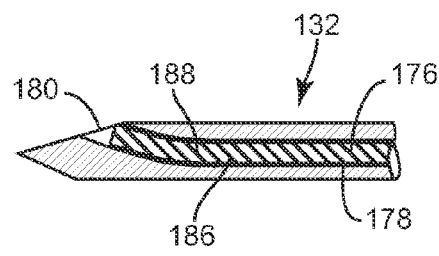
FIG. 17A is a cutaway, side cross section view of the distal end of the needle shown in FIG. 16 and one embodiment of a wire of the surgical instrument shown in FIG. 1.
Figure 17B:
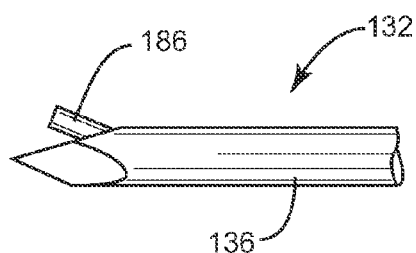
FIGS. 17B-17F are cutaway side views of the needle and the wire shown in FIG. 17A.
Figure 17C:
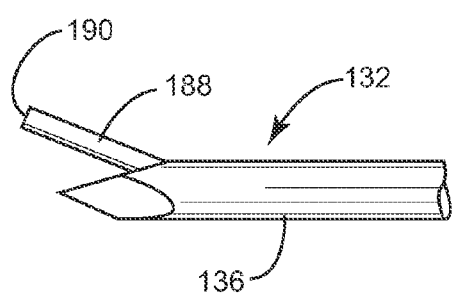
Figure 17D:
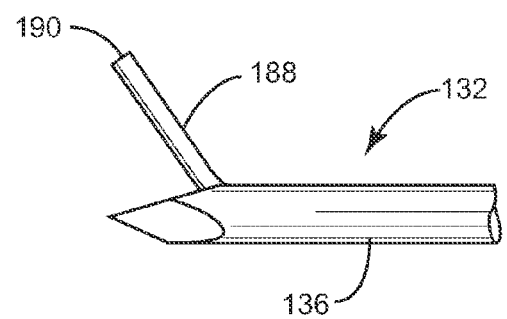
Figure 17E:
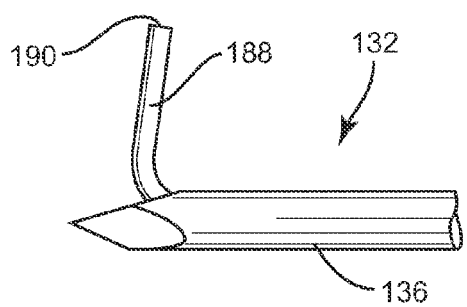
Figure 17F:
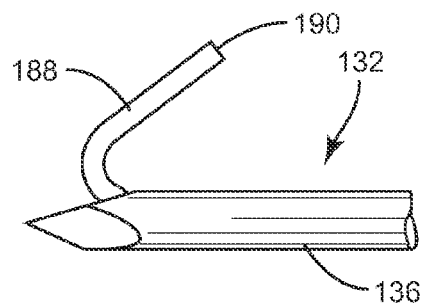
Figure 18A:
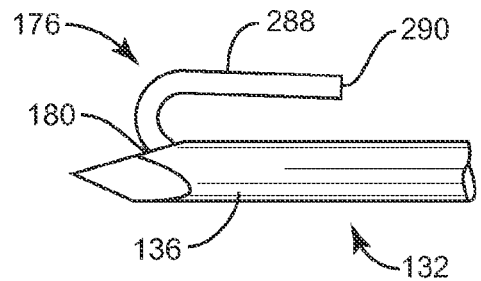
FIGS. 18A-18F are cutaway side views of the distal end of the needle shown in FIG. 16 and one embodiment of a wire of the surgical instrument shown in FIG. 1.
Figure 18B:
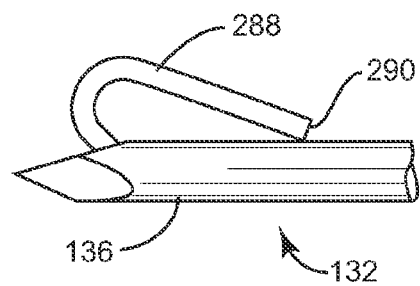
Figure 18C:
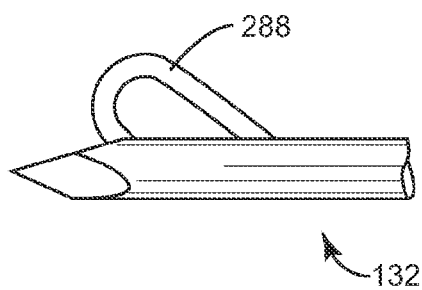
Figure 18D:
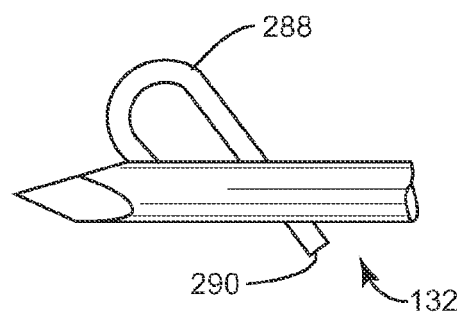
Figure 18E:
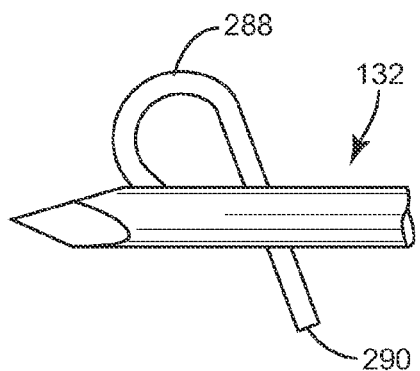
Figure 18F:
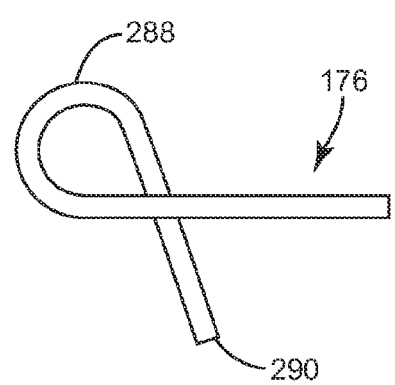

In one embodiment, as shown in FIGS. 16-17F, surgical delivery instrument 30, similar to that described with regard to FIGS. 1-15, includes a needle 132, similar to needle 32, having an elongated cavity, such as, for example, lumen 178 that defines an opening 180. A guide wire 176, similar to guide wire 76, is advanced along lumen 178 for assembly with needle 132. Guide wire 176 extends from a proximal end (not shown) to a distal end 186. Guide wire 176 includes a retainer, such as, for example, a flexible anchor 188. Anchor 188 is configured for disposal within lumen 178 and fixation with tissue, and includes a tip 190. Tip 190 has a blunt configuration and prevents undesired advancement of anchor 188 within tissue.

Within lumen 178, anchor 188 has a substantially linear configuration. Needle 132 is delivered to a desired location at a surgical site. Guide wire 176 is connected to an actuator (not shown), similar to trigger housing 48, for deployment of anchor 188.

Guide wire 176 is slidably moveable within lumen 178, relative to needle 132, from a first position (FIG. 17A) to a second position (FIG. 17F) such that anchor 188 is deployable with tissue. Guide wire 176 is movable via actuation with the actuator. It is contemplated that needle 132 remains stationary as distal end 186 exits opening 180. In the first position of guide wire 176, anchor 188 is disposed within lumen 178 in its first orientation. In the first orientation, anchor 188 is in a substantially linear configuration and disposed coaxial with a longitudinal axis of needle 132. Anchor 188 is elastically deformed and in a stressed condition to conform to lumen 178.

As guide wire 176 is actuated and moved to its second position, anchor 188 exits opening 180 and rotates about the length of guide wire 176 to its unstressed, natural configuration to form an expanded hook configuration in a second orientation of anchor 188. Anchor 188 rotates to the expanded hook configuration to frictionally engage tissue such that guide wire 176 is disposed in a fixed position with the tissue at a desired location at the surgical site. Blunt tip 190 prevents further advancement of anchor 188 within the tissue.

Needle 132 is removable from the surgical site such that guide wire 176 passes through lumen 178 leaving anchor 188 fixed at the surgical site and guide wire 176 within the protected passageway. Needle 132 remains engaged with the proximal end of guide wire 176. Surgical components can be advanced to a surgical site over guide wire 176 at a desired location and trajectory.

Upon completion of a surgical procedure or desired removal of distal end 186 from the surgical site, needle 132 is advanced along guide wire 176 such that distal end 136 is returned to the surgical site adjacent anchor 188. The actuator is manipulated such that guide wire 176 is retracted and anchor 188 is pulled or withdrawn from the tissue and released from frictional engagement therewith at the surgical site. Anchor 188 elastically deforms via engagement with lumen 178 adjacent opening 180. Anchor 188 moves from its second orientation to its first orientation, as described above, within lumen 178. Surgical delivery instrument 30, including needle 132 and guide wire 176, is removed or adjusted from the surgical site.

In one embodiment, as shown in FIGS. 18A-18F, surgical delivery instrument 30, similar to that described with regard to FIGS. 16-17F, includes needle 132 that defines lumen 178 having opening 180. Guide wire 176 is advanced along lumen 178 for assembly with needle 132. Guide wire 176 includes a retainer, such as, for example, a flexible anchor 288. Anchor 288 is flexibly configured for disposal within lumen 178 and fixation with tissue, and includes a tip 290. Tip 290 has a blunt configuration and prevents undesired advancement of anchor 288 within tissue.

Within lumen 178, anchor 288 has a substantially linear configuration. Needle 132 is delivered to a desired location at a surgical site. Guide wire 176 is slidably movable, relative to needle 132, from a first position, similar to that shown in FIG. 17A, to a second position (FIG. 18F) such that anchor 188 is deployable with tissue. In the first position of guide wire 176, anchor 288 is disposed within lumen 178 in its first orientation in a substantially linear configuration and disposed coaxial with the longitudinal axis of needle 132. In the first orientation, anchor 188 is elastically deformed and in a stressed condition to conform to lumen 178. As guide wire 176 is actuated and moved to its second position, anchor 288 exits opening 180, and rotates about the length of guide wire 176 to its unstressed, natural configuration to form an expanded loop configuration in a second orientation, as shown in FIGS. 18A-18F, of anchor 288. Anchor 288 rotates to the expanded loop configuration to frictionally engage tissue such that guide wire 176 is disposed in a fixed position with the tissue at a desired location at the surgical site. Blunt tip 290 prevents further advancement of anchor 288 within the tissue.

Needle 132 is removable from the surgical site such that guide wire 176 passes through lumen 178 leaving anchor 288 fixed at the surgical site and guide wire 176 within the protected passageway. Needle 132 remains engaged with the proximal end of guide wire 176. Surgical components can be advanced to a surgical site over guide wire 176 at a desired location and trajectory.

Upon completion of a surgical procedure or desired removal of distal end 186 from the surgical site, needle 132 is advanced along guide wire 176 such that distal end 136 is returned to the surgical site adjacent anchor 288. The actuator is manipulated such that guide wire 176 is retracted and anchor 288 is pulled or withdrawn from the tissue and released from frictional engagement therewith at the surgical site. Anchor 288 elastically deforms via engagement with lumen 178 adjacent opening 180. Anchor 288 moves from its second orientation to its first orientation, as described above, within lumen 178. Surgical delivery instrument 30, including needle 132 and guide wire 176, is removed or adjusted from the surgical site.

Figure 19:
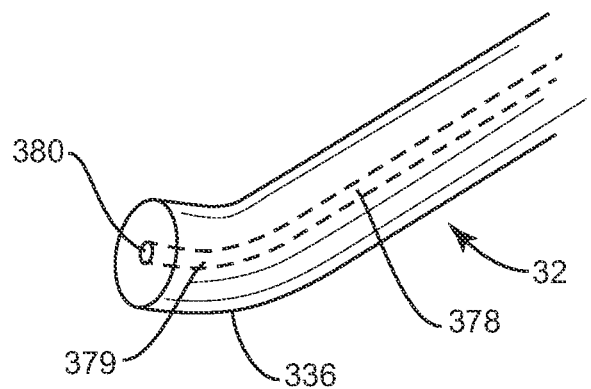
FIG. 19 is a cutaway perspective view of one embodiment of the distal end of the needle of the surgical instrument shown in FIG. 1.

In one embodiment, as shown in FIG. 19, surgical delivery instrument 30, similar that described with regard to FIGS. 1-15, includes needle 32 having an arcuate distal end 336. Distal end 336 has a blunt tip configuration. Needle 32 includes guide wire 76 (not shown) configured for relative slidable movement within an elongated cavity such as, for example, a lumen 378, similar to lumen 178 described with regard to FIGS. 16-18F. Lumen 378 is co-axial with the longitudinal axis of needle 32 and has an arcuate distal portion 379. Lumen 378 defines an opening 380 similar to openings 80, 180, adjacent the blunt tip of needle 32.

Figure 20:
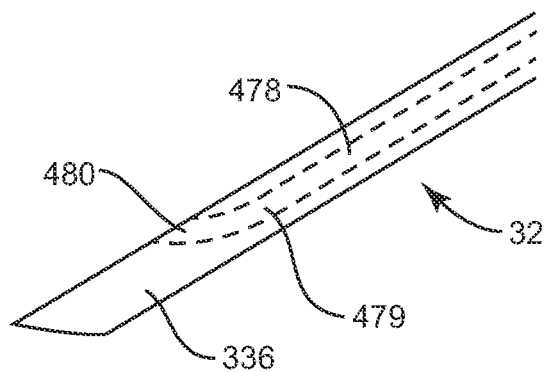
FIG. 20 is a cutaway perspective view of one embodiment of the distal end of the needle of the surgical instrument shown in FIG. 1.
Figure 21A:
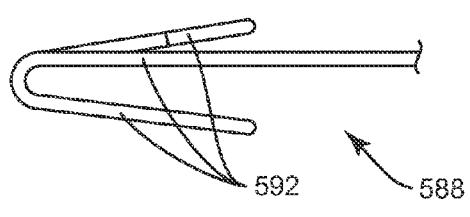
FIGS. 21A-21B are side cutaway views of one embodiment of the distal end of the wire shown in FIG. 6.
Figure 21B:
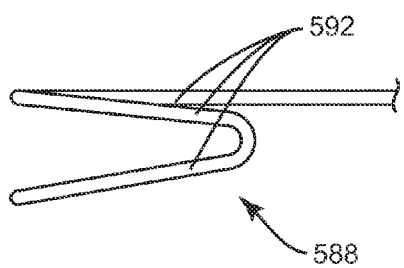
Figure 21C:
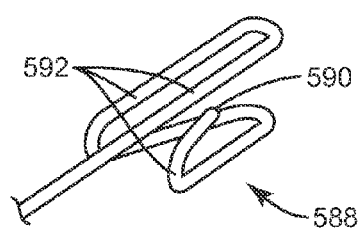
FIGS. 21C-21D are cutaway perspective views of the distal end shown in FIGS. 21A-21B.
Figure 21D:
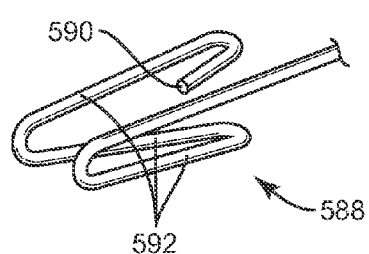

In one embodiment, as shown in FIG. 20, surgical delivery instrument 30, similar to that described with regard to FIGS. 1-15, includes needle 32 having guide wire 76 (not shown) configured for relative slidable movement within an elongated cavity, such as, for example, a lumen 478, similar to lumen 178 described with regard to FIGS. 16-18F. Lumen 478 is co-axial with the longitudinal axis of needle 32 and has an arcuate distal portion 479. Lumen 478 defines an opening 480 similar to openings 80, 180, disposed proximal to the distal end 336.

In one embodiment, as shown in FIGS. 21A-21D, surgical delivery instrument 30, similar to that described above, includes a guide wire, similar to guides wires 76, 176, having a retainer, such as for example, a flexible anchor 588, which is flexibly configured for disposal within a lumen, similar to lumens 78, 178, and fixation within tissue. Anchor 588 has a tip 590, which includes a blunt tip configuration and prevents undesired advancement of anchor 588 within tissue.

Anchor 588 is deployable from a first orientation to a second orientation. In its first orientation, anchor 588 is disposed within the lumen of the needle in a substantially linear configuration (not shown) and disposed co-axial with the longitudinal axis of the needle. In the first orientation, anchor 588 is elastically deformed and in a stressed condition to conform to the lumen.

As anchor 588 exits the opening adjacent the distal end of the needle, the linear configuration of anchor 588 rotates in multiple orientations about the length of the guide wire to its unstressed, natural configuration (shape memory) to form a multiple leg 592, expanded clip configuration in a second orientation, as shown in FIGS. 21A-21D. Anchor 588 rotates to the multiple leg, expanded clip configuration to frictionally engage tissue for disposal of the guide wire in a fixed position with the tissue at a desired location at the surgical site. Blunt tip 590 prevents further undesired advancement of anchor 588 within the tissue.

Upon completion of a surgical procedure or desired removal of anchor 588 from the surgical site, similar to that described with regard to FIGS. 16-18F, anchor 588 is pulled or withdrawn from the tissue and released from frictional engagement therewith at the surgical site. Anchor 588 elastically deforms via engagement with the needle lumen and moves from its second orientation to its first orientation, as described above.

It will be understood that various modifications may be made to the embodiments disclosed herein. Therefore, the above description should not be construed as limiting, but merely as exemplification of the various embodiments. Those skilled in the art will envision other modifications within the scope and spirit of the claims appended hereto.

What is claimed is:

1. A surgical instrument comprising:
a needle extending between a proximal end and a distal end, and defining a longitudinal axis, the needle including an elongated cavity that defines an opening disposed proximal to the distal end; and
a wire extending between a proximal end and a distal end configured for fixation with tissue, the proximal end of the wire extending parallel to the longitudinal axis and being movably disposed within the cavity, and the distal end of the wire being positioned outside of the cavity, the distal end of the wire being wrapped helically about the needle;
the distal end of the wire defines a retainer configured to prevent advancement of the retainer within the tissue, and wherein the elongated cavity is an open groove defined in an outer surface of the needle.

2. The surgical instrument of claim 1, wherein the needle further defines a reduced diameter portion disposed between the distal end of the needle and the opening, the reduced diameter portion being configured for disposal of the retainer.

3. The surgical instrument of claim 1, wherein the elongated cavity further defines an arcuate portion adjacent the opening.

4. The surgical instrument of claim 1, wherein the proximal end of the needle is connected with an actuator configured to deploy the wire such that the distal end of the wire fixes with the tissue.

5. The surgical instrument of claim 1, further comprising a sleeve disposed about the needle and being configured to retain the wire within the elongated cavity.

6. A surgical instrument comprising:
a needle extending between a proximal end and a distal end, and defining a longitudinal axis, the needle including an elongated cavity that defines an opening disposed proximal to the distal end; and
a guide wire extending between a proximal end and a distal end, the proximal end of the guide wire extending parallel to the longitudinal axis and being slidably disposed within the elongated cavity, the distal end of the guide wire including a flexible anchor wrapped helically about the needle, the distal end of the guide wire being positioned outside of the elongated cavity, wherein the flexible anchor is movable between a first orientation and a second orientation such that the anchor is expanded for removable fixation with tissue and in a configuration to prevent further advancement of the anchor within the tissue, wherein the needle defines an outer surface, the outer surface including the elongated cavity that is configured as an open groove.

7. The surgical instrument of claim 6, wherein the needle further defines a reduced diameter portion disposed between the distal end of the needle and the opening, the reduced diameter portion being configured for disposal of the anchor.

8. The surgical instrument of claim 7, wherein the anchor has an expandable coil configuration disposed circumferentially about the reduced diameter portion of the needle.

9. The surgical instrument of claim 6, further comprising a sleeve disposed about the needle and being configured to retain the guide wire within the elongated cavity.

10. The surgical instrument of claim 6, further comprising a handle connected to the needle, the handle including a safety element connected to the needle and movable between a first position such that the anchor is prevented from moving to the second orientation and a second position such that the anchor is free to move to the second orientation.

11. A surgical instrument comprising:
a needle extending between a proximal end and a distal end, and defining a longitudinal axis and an outer surface, the outer surface defining an open groove including an opening disposed proximal to the distal end;
a guide wire comprising a proximal end extending parallel to the longitudinal axis and being slidably disposed within the groove, the guide wire comprising a distal end including a flexible anchor having a blunt tip, the anchor being positioned outside of the cavity, the anchor being wrapped helically about the needle, the needle being movable between a first orientation such that the anchor is disposed in a collapsed configuration with the needle and a second, deployed orientation such that the anchor is expanded for fixation with tissue and the blunt tip is disposed to prevent further advancement of the anchor within the tissue;
a sleeve disposed about the needle; and
an actuator connected to the needle and the sleeve to effect movement of the needle between a first position such that the anchor is enclosed by the sleeve and a second position such that the anchor is free to move to the second orientation.

* * * * *